United States Patent [19]
Dumont

[11] 3,939,693
[45] Feb. 24, 1976

[54] PROCESS AND APPARATUS FOR THE QUALITATIVE AND QUANTITATIVE ANALYSIS OF SOLID MATERIAL
[75] Inventor: Philippe A. Dumont, Stokay St Georges, Belgium
[73] Assignee: Carrieres et Fours A Chaux Dumont-Wautier, Hermalle-sous-Huy, Belgium
[22] Filed: Apr. 18, 1974
[21] Appl. No.: 462,150

[30] Foreign Application Priority Data
Apr. 26, 1973  United Kingdom............... 19786/73

[52] U.S. Cl. .................................................... 73/19
[51] Int. Cl.² ........................................... G01N 7/16
[58] Field of Search ................................. 73/25, 19

[56] References Cited
UNITED STATES PATENTS
2,287,101   6/1942   Horvitz .................................... 73/25
FOREIGN PATENTS OR APPLICATIONS
1,278,762   9/1968   Germany ................................. 73/19

Primary Examiner—Herbert Goldstein
Assistant Examiner—Anthony V. Ciarlante
Attorney, Agent, or Firm—Kaufman & Kramer

[57] ABSTRACT

In a process and apparatus for measuring qualitatively and quantitatively at least one volatile fraction contained in a solid, a sample of a given weight of the solid is introduced in a first enclosure having a known internal capacity, the sample is then brought up to a temperature beyond the temperature at which said volatile fraction becomes gaseous in the first enclosure, the gasified volatile fraction is allowed to become distributed both in said first enclosure and in a second enclosure connected to the first enclosure, the second closed enclosure having previously been brought to a constant temperature having a known value which is higher than the temperature at which the gasified volatile fraction becomes liquid, and the pressure increase which occurs in the whole system due to the gasification of said volatile fraction is measured.

6 Claims, 2 Drawing Figures

PROCESS AND APPARATUS FOR THE QUALITATIVE AND QUANTITATIVE ANALYSIS OF SOLID MATERIAL

DESCRIPTION OF THE PRIOR ART

The ideal gas state equation based upon the Boyle-Mariotte and Gay-Lussac laws is as follows:

$$P.V. = n.R.T. \qquad (I)$$

wherein $P$ is the pressure in atmospheres exerted by a given gas, $V$ is the volume in liters occupied by said gas, $n$ is the number of moles of gas contained in the volume $V$, $R$ is the ideal gas constant and $T$ is the temperature of the gas in degrees K.

Various processes for the quantitative analysis of materials which are able to be converted into gases or are able to release gases either by action of heat or by chemical reaction with another material are based on equation (I).

Some of these processes are volumetric processes, wherein at known temperature and pressure, a proportionality is established between the volume occupied by the gas and the number of moles of the gas contained in said volume, as shown by the following equation:

$$V = K.n \qquad (II)$$

wherein $K = RT/P$

Among the known apparatus using said processes, the following ones may be cited:

1 the Orsat apparatus in which, by means of one or more selective absorptions of gases in solutions, it is possible to qualitatively and quantitatively analyse a mixture of several gases;

2 the Scheibler-Dietrich apparatus, in which it is possible to measure by volumetry the amount of calcium carbonate which is present in earth, minerals and rocks, the dissociation of calcium carbonate with formation of carbon dioxide being caused by an attack by means of an acid.

Other known processes are based on the proportionality between 1 the pressure exerted by a given gas which is produced within a constant volume, by reaction of the material to be analysed with another material and 2 the obtained number of gas moles, said processes being based on the following equation:

$$P = K.n \qquad (III)$$

wherein $K = RT/V$, $T$ and $V$ being known and generally constant during the test.

A known apparatus using this process is an apparatus in which it is possible to determine rapidly the water content of a material by chemical reaction of the present water with calcium carbide. In this case, acetylene is formed within a constant volume and the corresponding gas pressure is measured. Such an apparatus can only be used for determining the water content of a material, whereas the accuracy of the process is only approximate, since it depends on the nature of the material and on the porosity thereof, i.e. on the easiness with which the reaction between water and calcium carbide can take place.

BRIEF DESCRIPTION OF THE INVENTION

This invention relates to a process based on a new principle of analysing solid materials containing fractions which are able to be converted into a gas under the influence of heat, by sublimation, evaporation, dissociation or decomposition.

According to this invention, a sample of a given weight of the solid is introduced in a first enclosure having a known internal capacity, the sample is then brought up to a temperature beyond the temperature at which said volatile fraction becomes gaseous in the first enclosure, the gasified volatile fraction is allowed to become distributed both in said first enclosure and in a second enclosure connected to the first enclosure, the second closed enclosure having previously been brought to a constant temperature having a known value which is higher than the temperature at which the gasified volatile fraction becomes liquid and the pressure increase which occurs in the whole system due to the gasification of said volatile fraction is measured.

Under these circumstances, using the ideal gas state equation $$P = RT/V.n \qquad (IV)$$

a proportionality is established between the amount of formed gas ($n$) in the fixed volume ($V$) and the pressure ($P$) exerted by said gas.

To the best of applicant's knowledge, the principle described in the foregoing paragraph, which is a new application of the ideal gas state equation, has never been practically used, for the following reasons:

It is difficult to maintain, during the test, a sufficiently constant gas temperature at values of said temperature which are higher than the temperature of conversion of the solid material into a gas.

In most cases, the heat treatment of a solid material causes the release of several gases. For this reason, it is impossible to selectively measure the material to be analysed.

An object of this invention is to meet these drawbacks as follows:

- according to this invention, a constant value of the proportionality coefficient ($K$) is maintained in the ideal gas state equation as follows:

$$P = K.n \qquad (V)$$

wherein $K = RT/V$

- in the process and apparatus according to this invention, it is possible to measure quantitatively and selectively a single gas component of a mixture of several gases, by absorption of the other gaseous components.

As already pointed out, according to the process of this invention, a weighted sample of a solid material of the above type is introduced in a chamber or enclosure having a known volume ($V_1$), which is tightly closed and wherein said material is heated at a sufficient temperature ($T_1$) for causing at least one gas to be released by said material, said gas being allowed to flow into a second chamber or enclosure connected to the first chamber, said second chamber of known volume ($V_2$) being maintained at a constant temperature ($T_2$), the pressure created by the gas in the two chambers or enclosures being finally measured.

DETAILED DESCRIPTION OF THE PROCESS AND APPARATUS

Figure 1:
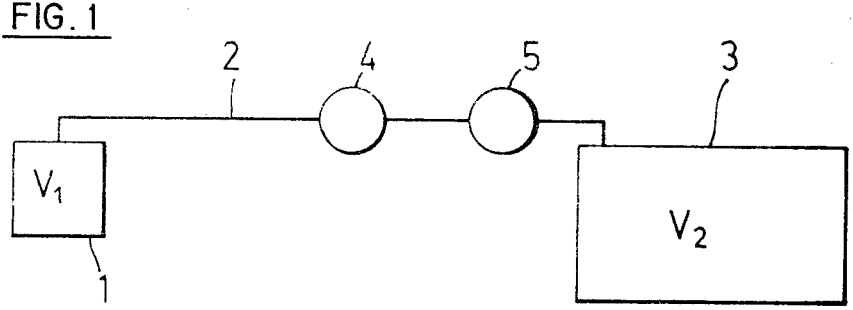
Figure 2:
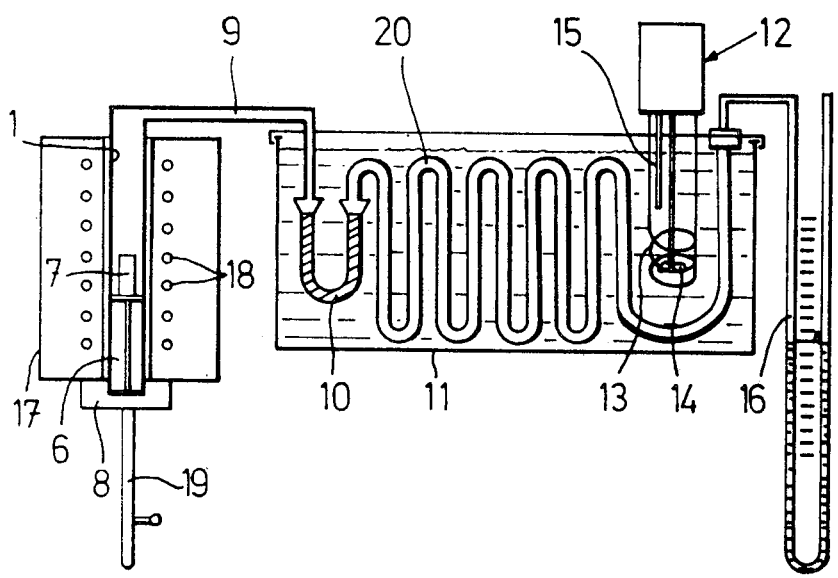

The process and apparatus according to this invention are respectively illustrated on FIGS. 1 and 2 of the attached drawings.

FIG. 1 shows a chamber 1 of a known volume $V_1$ in which the solid sample to be analysed is placed and heated at a temperature ($T_1$) which is sufficient to cause the solid material to be converted into one or more gases or to release one or more gases. Chamber 1 is connected by a capillary tube 2 to a second chamber 3 which has a known volume ($V_2$) and which is maintained at such a constant temperature ($T_2$) that the gas of which the pressure must be measured cannot condense in said chamber 3. The connection between the first chamber 1 and the second chamber 3 by means of a capillary tube 2 is necessary for reaching an equilibrium of the pressure in chambers 1 and 3.

Between the chambers 1 and 3, containers 4 and 5 are inserted in the connecting tube 2, each container 4, 5 containing an agent which is capable to absorb the secondary gases, i.e. the gaseous components which are released by the heat treatment of the solid sample and which are not to be analysed.

By suitable selecting the absorbent agents, it is possible to analyse selectively a single gas contained in a mixture of several gases produced by the heat treatment of the solid material.

The number of selective absorbing containers is not limited to two. One or more absorbing containers may be used. If the heat treatment of the solid material causes the release of a single gas, absorbing containers may of course be omitted.

For the type of apparatus schematically shown in FIG. 1, the ideal gas state equation which is true for small pressures of real gases can be written as follows:

When the process is started, chamber 1 which is at temperature $T_1$ is opened for introducing the solid sample therein. When chamber 1 is open, the pressure of the gas contained in chambers 1 and 3 is the atmospheric pressure.

In this case:
$$V_1 . P_a = n_{1a} . R . T_1 \quad \text{(VI)}$$
$$V_2 . P_a = n_{2a} . R . T_2 \quad \text{(VII)}$$

wherein $P_a$ is the atmospheric pressure, $n_{1a}$ is the number of gas moles contained in volume $V_1$ of chamber 1 and $n_{2a}$ is the number of gas moles contained in volume $V_2$ of chamber 3.

As soon as the sample has been introduced in chamber 1, this chamber is tightly closed.

Under the influence of the temperature $T_1$, a gas is released. This gas is distributed at the same pressure in volumes $V_1$ and $V_2$ and the following equations may then be written:
$$V_1 . (P_a + P_g) = (n_{1a} + n_{1g}) . R . T_1 \quad \text{(VIII)}$$
$$V_2 . (P_a + P_g) = (n_{2a} + n_{2g}) . R . T_2 \quad \text{(IX)}$$

wherein $P_g$ is the pressure of the gas released in volume $V_1$, $n_{1g}$ is the number of gas moles formed in volume $V_1$ and $n_{2g}$ is the number of gas moles formed in volume $V_2$.

Taking the values of $n_{1a}$ and $n_{2a}$ from equations (VI) and (VII), one obtains the following values:

$$n_{1a} = \frac{V_1 \cdot P_a}{R \cdot T_1}$$

$$n_{2a} = \frac{V_1 \cdot P_a}{R \cdot T_2} \quad \text{(X)}$$

When these values are replaced in equations (VIII) and (IX), the following equations are obtained:

$$V_1 (P_a + P_g) = \left( \frac{V_1 P_a}{R \cdot T_1} + n_{1g} \right) R \cdot T_1 \quad \text{(XI)}$$

$$V_2 (P_a + P_g) = \left( \frac{V_2 P_a}{R \cdot T_2} + n_{2g} \right) R \cdot T_2 \quad \text{(XII)}$$

These equations may be written as follows:

$$V_1 P_a + V_1 P_g = V_1 P_a + n_{1g} R . T_1$$

$$V_2 P_a + V_2 P_g = V_2 P_a + n_{2g} R . T_2$$

After simplification one has:

$$n_{1g} = \frac{V_1 P_g}{R \cdot T_1}$$

$$n_{2g} = \frac{V_2 P_g}{R \cdot T_2}$$

$$n_{1g} + n_{2g} = \frac{V_1 P_g}{R \cdot T_1} + \frac{V_2 P_g}{R \cdot T_2}$$

By reduction to the same denominator the value of $P_g$ can be obtained as follows:

$$n_{1g} + n_{2g} = n_g = \frac{V_1 T_2 P_g + V_2 T_1 P_g}{R T_1 T_2} \quad \text{(XIII)}$$

$$P_g = \frac{R T_1 T_2}{V_1 T_2 + V_2 T_1} n_g$$

From the comparison of equations (V) and (XIII), it appears that the accuracy of the process according to this invention depends on the knowledge of the value of K which, in equation (XIII), is equal to:

$$K = \frac{R \cdot T_1 \cdot T_2}{V_1 T_2 + V_2 T_1} \quad \text{(XIV)}$$

Since $R$, $V_1$ and $V_2$ are constants, the sole factors which have an influence on K are the temperatures $T_1$ and $T_2$.

According to this invention, the value of temperature $T_2$ in chamber 3 is maintained constant, whereas $T_1$ can be easily adjusted.

It is therefore clear that it is easily possible to determine the amount of gas ($n_g$) produced by heating the sample to be analysed by measuring the pressure ($P_g$) of this gas in $V_1$ and $V_2$.

This invention also relates to an apparatus for measuring qualitatively and quantitatively at least one volatile fraction contained in a solid.

In the lime burning industry, it is necessary to determine the calcium carbonate content of the quicklime obtained by decarbonation of limestone.

The major components of quicklime are calcium oxide ($CaO$), residual calcium carbonate ($CaCO_3$) and impurities, such as quartz grains, calcium silicates, iron oxides, alumina and magnesia.

The quantitative analysis of the residual calcium carbonate has been made in the past by various methods using several apparatuses. All these methods are based on the analysis of the carbon dioxide obtained by heat decomposition or by acid attack.

Among the known apparatuses the following may be cited:

1. Orsat-Dietrich-Fruelhing apparatus and Scheibler-Dietrich apparatus, in which the volume of released carbon dioxide is measured.

2. Schroeder apparatus in which the loss of weight due to the release of carbon dioxide obtained by treating the carbonate by means of an acid is measured.

3. Various apparatuses in which the weight increase of a selective carbon dioxide absorbent is measured.

4. Apparatus in which the carbon dioxide is absorbed in a solution of barium perchlorate with formation of barium carbonate, this reaction involving a pH decrease which is coulometrically titrated.

5. Apparatus measuring the variation of heat conductivity of a carrier gas (such as nitrogen) when mixed with carbon dioxide.

6. Apparatus using infrared spectrophotometry.

All these known apparatuses have one or more drawbacks such as complexity of handling to be done by qualified and skilled people, excessive duration of analysis, high cost of the apparatus, lack of accuracy of the analysis.

This invention relates to an apparatus which does not have such drawbacks.

According to this invention, the apparatus comprises a furnace, a first enclosure or chamber in said furnace, adapted for receiving a sample of a given weight of the solid and having means for closing it in a tight manner, a second enclosure or chamber connected to the first enclosure of chamber, a device for maintaining a constant temperature in the second enclosure or chamber and means for measuring the pressure developed within the two enclosures or chambers.

According to an additional feature of this invention, the volume or capacity of the second enclosure is larger than that of the first chamber.

The apparatus according to this invention may also contain means for inserting samples of materials to be tested in the first chamber and for removing said samples from this chamber, as well as means for absorbing one or more secondary gases not to be analysed, said latter means being located between the first chamber and the second chamber.

An embodiment of an apparatus according to this invention will now be described with reference to FIG. 2 of the attached drawings.

The apparatus diagrammatically shown in FIG. 2 comprises a tubular oven 17 having a chamber 1 which can be heated by means of an electrical resistance 18. A piston 6 carrying a crucible 7 containing a sample of solid material to be analysed can be inserted into chamber 1, said piston 6 being attached to a closure member 8 provided with a vertical handle 19. The closure member 8 may be of the bayonet type, so as to enable a tight closure of chamber 1. At the upper end of chamber 1, which may be a quartz tube, said chamber is connected by a capillary tube 9 to a U-shaped tube 10 containing an absorbent agent for a secondary gas (such as water vapor). The U-shaped absorbing tube 10 is connected to a tube coil 20 which forms together with said U-shaped tube 10 a second chamber, the volume of which is larger than that of the first chamber 1.

The U-shaped tube 10 and coil 20 are located in a container 11 containing a thermostatic bath which may be a water bath or a bath of another liquid. Said bath is maintained at a constant temperature by means of a thermostatic heater 12 comprising a heating wire 13, a stirrer 14 and a thermometer 15.

The tube coil 20 is connected to a capillary U-shaped tube 16 containing a manometric liquid for measuring the pressure of the gas released from the sample to be analysed.

The following example illustrates the process according to this invention.

EXAMPLE

The calcium carbonate content of samples of quicklime has been determined by means of the above described apparatus having the following characteristics:
$V_1$ = volume of first chamber: 0.18 liters
$V_2$ = volume of second chamber: 1.35 liters
$T_1$ = temperature in first chamber: 1100°C ± 100°C
$T_2$ = temperature in second chamber: 30°C ± 0.1°C Samples of 5 grams of quicklime containing about 2% of calcium carbonate have been placed in chamber 1. The test has been repeated ten times. In each case the measured content of calcium carbonate has been of 2% ± 0.0133%.

The duration of each test was of about 10 minutes. This duration can of course be decreased by increasing the temperature $T_1$ in the first chamber.

The apparatus according to this invention only needs the weighing of samples of the materials to be analysed and can therefore be serviced by unskilled people. The analysis can be performed with heavy samples (5 grams or more) so as to reduce substantially the weighing error and to work with representative samples.

The apparatus comprises only ordinary and cheap components. It can be made automatic by using a mechanical system for introducing the samples to be analysed in the first chamber 1 and for removing the samples therefrom and by using an electronic or other system for recording the results of the analysis.

The method and apparatus according to this invention may be used for analysing all solid materials which, under the influence of heat, can be sublimated, evaporated or dissociated so as to release at least one gaseous component. They can therefore be used in various industries, such as the lime burning, cement, plaster and road building industries. They can also be used for determining the water content of solids. In the latter case, the volume $V_2$ of the second chamber as well as the capillary tubes 9 and 16 must be kept at a temperature of more than 100°C, so as to maintain the water in gaseous phase.

As already pointed out, the process and the apparatus according to this invention may be used for the qualitative and quantitative analysis of samples containing several materials capable of releasing several gases. For example, when using a mixture of gypsum, plaster and anhydrite, it is possible to follow the increase of pressure as a function of the increase of temperature $T_1$, taking into account the increase of pressure due to the increase of $T_1$.

It is to be noted that the sensitivity and the accuracy of the measures depend on the stability of temperatures $T_1$ and $T_2$, on the amounts of the analysed samples and on the ratio of the volumes $V_2$ and $V_1$. These factors can be freely selected by the user for meeting particular purposes.

I claim:

1. Process for measuring qualitatively and quantitatively at least one volatile fraction contained in a solid, in which a sample of a given weight of the solid is introduced in a first enclosure having a known internal capacity, the sample is then brought up to a temperature at which said volatile fraction becomes gaseous in the first enclosure, the gasified volatile fraction is allowed to become distributed both in said first enclosure and in a second enclosure connected to the first enclosure by a capillary tube and having a higher internal capacity than the first enclosure, the second enclosure having previously been brought to a constant temperature having a known value which is higher than the temperature at which the gasified volatile fraction become liquid but lower than the temperature reached in the first enclosure, the pressure increase which occurs in the whole system due to the gasification of said volatile fraction is measured and gas state equations for said enclosures are solved.

2. Process according to claim 1, in which at least one secondary gas is absorbed during the distribution of the gasified volatile fraction among the two enclosures.

3. Apparatus for measuring qualitatively and quantitatively at least one volatile fraction contained in a solid, comprising a furnace, a first enclosure or chamber of a given capacity in said furnace, adapted for receiving a sample of a given weight of the solid and having means for closing it in a tight manner, a second enclosure of chamber of a higher capacity than the first enclosure and connected to the first enclosure or chamber by means of a capillary tube, a device for maintaining in the second enclosure or chamber a constant temperature which is lower than the temperature reached in the first enclosure, and means for measuring the pressure developed within the two enclosures or chambers.

4. Apparatus according to claim 3, including also at least one device for absorbing secondary gases.

5. Apparatus according to claim 3, in which the second enclosure is a pipe coil.

6. Apparatus according to claim 5, in which the pipe coil is immersed in a thermostatic bath which is the device for maintaining a constant temperature in the coil.

* * * * *